US008435516B2

(12) United States Patent
Huang et al.

(10) Patent No.: US 8,435,516 B2
(45) Date of Patent: May 7, 2013

(54) CANCER TREATMENT

(75) Inventors: Bo Huang, New London, CT (US);
Margaret Ann Marshall, Waterford, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 13/501,730

(22) PCT Filed: Oct. 4, 2010

(86) PCT No.: PCT/IB2010/054465
§ 371 (c)(1),
(2), (4) Date: Apr. 12, 2012

(87) PCT Pub. No.: WO2011/045704
PCT Pub. Date: Apr. 21, 2011

(65) Prior Publication Data
US 2012/0213793 A1 Aug. 23, 2012

Related U.S. Application Data

(60) Provisional application No. 61/250,711, filed on Oct. 12, 2009.

(51) Int. Cl.
*A61K 39/395* (2006.01)
*G01N 33/53* (2006.01)
(52) U.S. Cl.
USPC .......................................... 424/130.1; 435/7.1
(58) Field of Classification Search .................. None
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,397 | A | 3/1989 | Boss et al. |
| 4,816,567 | A | 3/1989 | Cabilly et al. |
| 5,703,057 | A | 12/1997 | Johnston et al. |
| 5,770,429 | A | 6/1998 | Lonberg et al. |
| 5,916,771 | A | 6/1999 | Hori et al. |
| 6,602,684 | B1 | 8/2003 | Umana et al. |
| 6,682,736 | B1 | 1/2004 | Hanson et al. |
| 6,984,720 | B1 | 1/2006 | Korman et al. |
| 2003/0157108 | A1 | 8/2003 | Presta |
| 2003/0207336 | A1 | 11/2003 | Jardieu et al. |
| 2003/0207346 | A1 | 11/2003 | Arathoon et al. |
| 2004/0063911 | A1 | 4/2004 | DeFrees et al. |
| 2004/0072290 | A1 | 4/2004 | Umana et al. |
| 2004/0120948 | A1 | 6/2004 | Mikayama et al. |
| 2004/0132640 | A1 | 7/2004 | DeFrees et al. |
| 2004/0142856 | A1 | 7/2004 | DeFrees et al. |
| 2012/0220640 | A1* | 8/2012 | Ashdown et al. ............. 514/393 |

FOREIGN PATENT DOCUMENTS

| | | |
|---|---|---|
| EP | 216846 | 1/1990 |
| EP | 256055 | 8/1991 |
| EP | 323997 | 4/1993 |
| EP | 338841 | 3/1995 |
| WO | WO 93/00431 | 1/1993 |
| WO | WO 98/58964 | 12/1998 |
| WO | WO 99/22764 | 5/1999 |
| WO | WO 00/24893 | 5/2000 |
| WO | WO 00/32231 | 6/2000 |
| WO | WO 00/37504 | 6/2000 |
| WO | WO 01/14424 | 3/2001 |
| WO | WO 01/81405 | 11/2001 |
| WO | WO 03/031464 | 4/2003 |

OTHER PUBLICATIONS

Altschul et al., "Basic Local Alignment Search Tool," J. Mol. Biol. 215:403-410, Academic Press (1990).
Altschul et al., "Gapped BLAST and PSI-BLAST: A New Generation of Protein Database Search Programs," Nucleic Acids Res. 25:3389-3402 Oxford University Press (1997).
Barnes et al., "Characterization of the Stability of Recombinant Protein Production in the GS-NS0 Expression System," Biotech & Bioengineering 73:261-270 John Wiley and Sons, Inc. (2001).
Blay et al., "Serum Level of Interleukin 6 as a Prognosis Factor in Metastatic Renal Cell Carcinoma," Cancer Res. 52:3317-3322 American Association for Cancer Research (1992).
Chothia et al., "Canonical Structures for the Hypervariable Regions of Immunoglobulins," J. Mol. Biol. 196:901-917 (1987).
Clarke et al, "A Phase I, Pharmacokinetic (PK), and Preliminary Efficacy Assessment of ALD518, a Humanized Anti-IL-6 Antibody, in Patients with Advanced Cancer," J. Clin. Oncol. 27:15s (2009) (suppl; abstr 3025).
Comin-Anduix et al., "Detailed analysis of immunologic effects of the cytotoxic T lymphocyte-associated antigen 4-blocking monoclonal antibody tremelimumab in peripheral blood of patients with melanoma," Journal of Translational Medicine, Biomed Central, 6(1):22 (2008).
Deichmann et al., "Interleukin-6 and its surrogate C-reactive protein are useful serum markers for monitoring metastasized malignant melanoma," Journal of Experimental & Clinical Cancer Research, 19(3):301-307 (2000).
Deichmann et al., "Diagnosing Melanoma Patients Entering American Joint Committee on Cancer Stage IV, C-Reactive Protein in Serum is Superior to Lactate Dehydrogenase," British Journal of Cancer 91:699-702 Cancer Research UK (2004).

(Continued)

*Primary Examiner* — Ilia Ouspenski
(74) *Attorney, Agent, or Firm* — Ropes & Gray LLP; Jane T. Gunnison; Z. Ying Li

(57) ABSTRACT

The present invention relates to methods of treating cancer, such as melanoma, by administering a CTLA4 antagonist to a subject with a serum C-Reactive Protein (CRP) concentration that is less than or equal to some amount. The invention further relates to methods of treating cancer by determining the level of serum CRP concentration in a subject, and then administering a CTLA4 antagonist if the CRP concentration is less than or equal to a certain amount. The invention further relates to, among other things, the use of serum CRP concentration as a predictive factor for a subjects response to a cancer treatment.

14 Claims, 2 Drawing Sheets

OTHER PUBLICATIONS

Erlandsen et al., "Reference Interval for Serum C-Reactive Protein in Healthy Blood Donors Using the Dade Behring N Latex CRP Mono Assay," Scand. J. Clin. Lab Invest. 60:37-43 (2000).

Erlinger et al., "C-reactive protein and the risk of incident colorectal cancer," JAMA: The Journal of the American Medical Association, 291(5):585-590 (2004).

Falconer et al., "Acute-Phase Protein Response and Survival Duration of Patients with Pancreatic Cancer," Cancer 75:2077-2082 (1995).

Findeisen et al., "Serum amyloid A as a prognostic marker in melanoma identified by proteomic profiling," Journal of Clinical Oncology, 27(13):2199-2208 (2009).

Gough et al., "Metabolic Disturbance and Sensitivity to Endotoxin in Patients with Advanced Cancer: Relationship to Lymphocyte Reactivity, Tumour Necrosis Factor (TNF) Production and Survival," Clin. Exp. Immunol. 105:529-536 Blackwell Science (1996).

Guida et al., "Fibrinogen: a novel predictor of responsiveness in metastatic melanoma patients treated with bio-chemotherapy: IMI (italian melanoma inter-group) trial," Journal of Translational Medicine 1(1):13 (2003).

Hakimuddin et al., "A Chemical Method for the Deglycosylation of Proteins," Arch. Biochem. Biophys. 259:52-57 (1987).

Kuroiwa at al., "Manipulations of Human Minichromosomes to Carry Greater than Megabase-Sized Chromosome Inserts," Nature Biotechnol. 18:1086-1090 (2000).

Kwon et al., "Elimination of Residual Metastatic Prostate Cancer After Surgery and Adjunctive Cytotoxic T Lymphocyte-Associated Antigen 4 (CTLA-4) Blockade Immunotherapy," Proc. Natl. Acad. Sci. USA 96:15074-15079 (1999).

Kwon et al., "Manipulation of T Cell Costimulatory and Inhibitory Signals for Immunotherapy of Prostate Cancer," Proc. Natl. Acad. Sci. USA 94:8099-8103 (1997).

Leach et al., "Enhancement of Antitumor Immunity by CTLA-4 Blockade," Science 271:1734-1736 (1996).

Lonberg et al., "Antigen-Specific Human Antibodies from Mice Comprising Four Distinct Genetic Modifications," Nature 368:856-859 (1994).

Mage et al., "Preparation of Fab and F(ab')$_2$ Fragments from Monoclonal Antibodies, Monoclonal Antibody Production Techniques and Applications," pp. 79-97, Marcel Dekker, Inc., New York, NY (1987).

Mahmoud et al., "The role of C-reactive protein as a prognostic indicator in advanced cancer," Current Oncology Reports, 4(3):250-255 (2002).

McCoy et al., "The Role of CTLA-4 in the Regulation of T Cell Immune Responses," Immunol. & Cell Bio. 77:1-10 (1999).

Moses et al., "Pro-inflammatory Cytokine Release by Peripheral Blood Mononuclear Cells from Patients with Advanced Pancreatic Cancer: Relationship to Acute Phase Response and Survival," Oncology Reports 21:1091-1095 (2009).

Mukherjee et al., "Modulation of cell cycle progression by CTLA4-CD80/CD86 interactions on CD4+ T cells depends on strength of the CD3 signal: critical role for IL-2," Journal of Leukocyte Biology 80(1):66-74 (2006).

Pearson, "Flexible Sequence Similarity Searching with the FASTA3 Program Package," Methods Mol. Biol. 132:185-219 (2000).

Pearson, "Rapid and Sensitive Sequence Comparison with FASTP and FASTA," Methods Enzymol. 183:63-98 (1990).

Pepys et al., "C-Reactive Protein: a Critical Update," J. Clin. Invest. 111(12):1805-1812 (2003).

Reichle et al., "Pioglitazone and rofecoxib combined with angiostatically scheduled trofosfamide in the treatment of far-advanced melanoma and soft tissue sarcoma," Cancer, 101(10):2247-2256 (2004).

Tartour et al., "Serum interleukin 6 and C-reactive protein levels correlate with resistance to IL-2 therapy and poor survival in melanoma patients," British Journal of Cancer, 69(5):911-913 (1994).

Tas Faruk et al., "The value of serum levels of IL-6, TNF-alpha, and erythropoietin in metastatic malignant melanoma: serum IL-6 level is a valuable prognostic factor at least as serum LDH in advanced melanoma," Medical Oncology 22(3):241-246 (2005).

Thompson et al., "The Emerging Role of CTLA-4 as an Immune Attenuator," Immunity, 7:445-450 (1997).

Thotakura et al., "Enzymatic Deglycosylation of Glycoproteins," Meth. Enzymol., 138:350-359 (1987).

Tomizuka et al., "Double Trans-Chromosomic Mice: Maintenance of Two Individual Human Chromosome Fragments Containing LG Heavy and K Loci and Expression of Fully Human Antibodies," Proc. Natl. Acad. Sci. USA, 97:722-727 (2000).

Wang et al., "C-reactive protein and malignancy: clinic-pathological association and therapeutic implication," Chang Gung Medical Journal 32(51:471-482 (2009).

Ward et al., "Binding Activities of a Repertoire of Single Immunoglobulin Variable Domains Secreted from *Escherichia coli*," Nature 341:544-546 (1989).

Weber et al., "A randomized, double-blind, placebo-controlled, phase II study comparing the tolerability and efficacy of ipilimumab administered with or without prophylactic budesonide in patients with unresectable stage III or IV melanoma," Clinical Cancer Research 15(17):5591-5598 (2009).

Winter et al., "Humanized Antibodies," Immunol. Today 14:243-246 (1993).

Wright et al., "Genetically Engineered Antibodies: Progress and Prospects," Crit. Reviews in Immunol. 12:125-168 (1992).

* cited by examiner

SEQUENCE LISTING

<160> NUMBER OF SEQ ID NOS: 32

<210> SEQ ID NO 1
<211> LENGTH: 10
<212> TYPE: PRT
<213> ORGANISM: Homo sapiens

<400> SEQUENCE: 1

Gly Phe Thr Phe Ser Ser His Gly Met His
1               5                   10

<210> SEQ ID NO 2
<211> LENGTH: 15
<212> TYPE: PRT
<213> ORGANISM: Homo sapiens

<400> SEQUENCE: 2

Val Ile Trp Tyr Asp Gly Arg Asn Lys Tyr Tyr Ala Asp Ser Val
1               5                   10                  15

<210> SEQ ID NO 3
<211> LENGTH: 9
<212> TYPE: PRT
<213> ORGANISM: Homo sapiens

<400> SEQUENCE: 3

Gly Gly His Phe Gly Pro Phe Asp Tyr
1               5

```
<210> SEQ ID NO 4
<211> LENGTH: 12
<212> TYPE: PRT
<213> ORGANISM: Homo sapiens

<400> SEQUENCE: 4

Arg Ala Ser Gln Ser Ile Ser Ser Ser Phe Leu Ala
1               5                   10

<210> SEQ ID NO 5
<211> LENGTH: 7
<212> TYPE: PRT
<213> ORGANISM: Homo sapiens

<400> SEQUENCE: 5

Gly Ala Ser Ser Arg Ala Thr
1               5

<210> SEQ ID NO 6
<211> LENGTH: 10
<212> TYPE: PRT
<213> ORGANISM: Homo sapiens

<400> SEQUENCE: 6

Cys Gln Gln Tyr Gly Thr Ser Pro Trp Thr
1               5                   10

<210> SEQ ID NO 7
<211> LENGTH: 167
<212> TYPE: PRT
<213> ORGANISM: Homo sapiens

<400> SEQUENCE: 7

Gly Val Val Gln Pro Gly Arg Ser Leu Arg Leu Ser Cys Val Ala Ser
1               5                   10                  15

Gly Phe Thr Phe Ser Ser His Gly Met His Trp Val Arg Gln Ala Pro
            20                  25                  30

Gly Lys Gly Leu Glu Trp Val Ala Val Ile Trp Tyr Asp Gly Arg Asn
        35                  40                  45

Lys Tyr Tyr Ala Asp Ser Val Lys Gly Arg Phe Thr Ile Ser Arg Asp
    50                  55                  60

Asn Ser Lys Asn Thr Leu Phe Leu Gln Met Asn Ser Leu Arg Ala Glu
65                  70                  75                  80

Asp Thr Ala Val Tyr Tyr Cys Ala Arg Gly His Phe Gly Pro Phe
                85                  90                  95

Asp Tyr Trp Gly Gln Gly Thr Leu Val Thr Val Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln
                165

<210> SEQ ID NO 8
<211> LENGTH: 141
<212> TYPE: PRT
<213> ORGANISM: Homo sapiens
```

```
<400> SEQUENCE: 8

Gln Ser Pro Gly Thr Leu Ser Leu Ser Pro Gly Glu Arg Ala Thr Leu
1               5                   10                  15

Ser Cys Arg Ala Ser Gln Ser Ile Ser Ser Ser Phe Leu Ala Trp Tyr
            20                  25                  30

Gln Gln Arg Pro Gly Gln Ala Pro Arg Leu Leu Ile Tyr Gly Ala Ser
        35                  40                  45

Ser Arg Ala Thr Gly Ile Pro Asp Arg Phe Ser Gly Ser Gly Ser Gly
    50                  55                  60

Thr Asp Phe Thr Leu Thr Ile Ser Arg Leu Glu Pro Glu Asp Phe Ala
65                  70                  75                  80

Val Tyr Tyr Cys Gln Gln Tyr Gly Thr Ser Pro Trp Thr Phe Gly Gln
                85                  90                  95

Gly Thr Lys Val Glu Ile Lys Arg Thr Val Ala Ala Pro Ser Val Phe
            100                 105                 110

Ile Phe Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys
    130                 135                 140

<210> SEQ ID NO 9
<211> LENGTH: 10
<212> TYPE: PRT
<213> ORGANISM: Homo sapiens

<400> SEQUENCE: 9

Gly Phe Thr Phe Ser Ser His Gly Ile His
1               5                   10

<210> SEQ ID NO 10
<211> LENGTH: 15
<212> TYPE: PRT
<213> ORGANISM: Homo sapiens

<400> SEQUENCE: 10

Val Ile Trp Tyr Asp Gly Arg Asn Lys Asp Tyr Ala Asp Ser Val
1               5                   10                  15

<210> SEQ ID NO 11
<211> LENGTH: 9
<212> TYPE: PRT
<213> ORGANISM: Homo sapiens

<400> SEQUENCE: 11

Val Ala Pro Leu Gly Pro Leu Asp Tyr
1               5

<210> SEQ ID NO 12
<211> LENGTH: 11
<212> TYPE: PRT
<213> ORGANISM: Homo sapiens

<400> SEQUENCE: 12

Arg Ala Ser Gln Ser Val Ser Ser Tyr Leu Ala
1               5                   10

<210> SEQ ID NO 13
<211> LENGTH: 7
<212> TYPE: PRT
<213> ORGANISM: Homo sapiens
```

<400> SEQUENCE: 13

Gly Ala Ser Ser Arg Ala Thr
1               5

<210> SEQ ID NO 14
<211> LENGTH: 10
<212> TYPE: PRT
<213> ORGANISM: Homo sapiens

<400> SEQUENCE: 14

Cys Gln Gln Tyr Gly Arg Ser Pro Phe Thr
1               5                   10

<210> SEQ ID NO 15
<211> LENGTH: 153
<212> TYPE: PRT
<213> ORGANISM: Homo sapiens

<400> SEQUENCE: 15

Pro Gly Arg Ser Leu Arg Leu Ser Cys Ala Ala Ser Gly Phe Thr Phe
1               5                   10                  15

Ser Ser His Gly Ile His Trp Val Arg Gln Ala Pro Gly Lys Gly Leu
            20                  25                  30

Glu Trp Val Ala Val Ile Trp Tyr Asp Gly Arg Asn Lys Asp Tyr Ala
        35                  40                  45

Asp Ser Val Lys Gly Arg Phe Thr Ile Ser Arg Asp Asn Ser Lys Asn
    50                  55                  60

Thr Leu Tyr Leu Gln Met Asn Ser Leu Arg Ala Glu Asp Thr Ala Val
65                  70                  75                  80

Tyr Tyr Cys Ala Arg Val Ala Pro Leu Gly Pro Leu Asp Tyr Trp Gly
                85                  90                  95

Gln Gly Thr Leu Val Thr Val Ser Ser Ala Ser Thr Lys Gly Pro Ser
            100                 105                 110

Val Phe Pro Leu Ala Pro Cys Ser Arg Ser Thr Ser Glu Ser Thr Ala
        115                 120                 125

Ala Leu Gly Cys Leu Val Lys Asp Tyr Phe Pro Glu Pro Val Thr Val
    130                 135                 140

Ser Trp Asn Ser Gly Ala Leu Thr Ser
145                 150

<210> SEQ ID NO 16
<211> LENGTH: 146
<212> TYPE: PRT
<213> ORGANISM: Homo sapiens

<400> SEQUENCE: 16

Gln Ser Pro Gly Thr Leu Ser Leu Ser Pro Gly Glu Arg Ala Thr Leu
1               5                   10                  15

Ser Cys Arg Ala Ser Gln Ser Val Ser Ser Tyr Leu Trp Tyr Gln
            20                  25                  30

Gln Lys Pro Gly Gln Ala Pro Arg Leu Leu Ile Tyr Gly Ala Ser Ser
        35                  40                  45

Arg Ala Thr Gly Ile Pro Asp Arg Phe Ser Gly Ser Gly Ser Gly Thr
    50                  55                  60

Asp Phe Thr Leu Thr Ile Ser Arg Leu Glu Pro Glu Asp Phe Ala Val
65                  70                  75                  80

Tyr Tyr Cys Gln Gln Tyr Gly Arg Ser Pro Phe Thr Phe Gly Pro Gly
                85                  90                  95

```
Thr Lys Val Asp Ile Lys Arg Thr Val Ala Ala Pro Ser Val Phe Ile
                100                 105                 110

Phe Pro Pro Ser Asp Glu Gln Leu Lys Ser Gly Thr Ala Ser Val Val
            115                 120                 125

Cys Leu Leu Asn Asn Phe Tyr Pro Arg Glu Ala Lys Val Gln Trp Lys
130                 135                 140

Val Asp
145

<210> SEQ ID NO 17
<211> LENGTH: 10
<212> TYPE: PRT
<213> ORGANISM: Homo sapiens

<400> SEQUENCE: 17

Gly Phe Thr Phe Ser Ser Tyr Gly Met His
1               5                   10

<210> SEQ ID NO 18
<211> LENGTH: 15
<212> TYPE: PRT
<213> ORGANISM: Homo sapiens

<400> SEQUENCE: 18

Val Ile Trp Tyr Asp Gly Ser Asn Lys Tyr Tyr Ala Asp Ser Val
1               5                   10                  15

<210> SEQ ID NO 19
<211> LENGTH: 24
<212> TYPE: PRT
<213> ORGANISM: Homo sapiens

<400> SEQUENCE: 19

Thr Ala Val Tyr Tyr Cys Ala Arg Asp Pro Arg Gly Ala Thr Leu Tyr
1               5                   10                  15

Tyr Tyr Tyr Tyr Gly Met Asp Val
            20

<210> SEQ ID NO 20
<211> LENGTH: 11
<212> TYPE: PRT
<213> ORGANISM: Homo sapiens

<400> SEQUENCE: 20

Arg Ala Ser Gln Ser Ile Asn Ser Tyr Leu Asp
1               5                   10

<210> SEQ ID NO 21
<211> LENGTH: 7
<212> TYPE: PRT
<213> ORGANISM: Homo sapiens

<400> SEQUENCE: 21

Ala Ala Ser Ser Leu Gln Ser
1               5

<210> SEQ ID NO 22
<211> LENGTH: 9
<212> TYPE: PRT
<213> ORGANISM: Homo sapiens

<400> SEQUENCE: 22

Gln Gln Tyr Tyr Ser Thr Pro Phe Thr
1               5
```

```
<210> SEQ ID NO 23
<211> LENGTH: 167
<212> TYPE: PRT
<213> ORGANISM: Homo sapiens

<400> SEQUENCE: 23

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
130                 135                 140

Val Lys Asp Tyr Phe Pro Glu Pro Val Thr Val Ser Trp Asn Ser Gly
145                 150                 155                 160

Ala Leu Thr Ser Gly Val His
            165

<210> SEQ ID NO 24
<211> LENGTH: 139
<212> TYPE: PRT
<213> ORGANISM: Homo sapiens

<400> SEQUENCE: 24

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

Pro Gly Lys Ala Pro Lys Leu Leu Ile Tyr Ala Ala Ser Ser Leu Gln
        35                  40                  45

Ser Gly Val Pro Ser Arg Phe Ser Gly Ser Gly Ser Gly Thr Asp Phe
50                  55                  60

Thr Leu Thr Ile Ser Ser Leu Gln Pro Glu Asp Phe Ala Thr Tyr Tyr
65                  70                  75                  80

Cys Gln Gln Tyr Tyr Ser Thr Pro Thr Phe Gly Pro Gly Thr Lys
                85                  90                  95

Val Glu Ile Lys Arg Thr Val Ala Ala Pro Ser Val Phe Ile Phe Pro
            100                 105                 110

Pro Ser Asp Glu Gln Leu Lys Ser Gly Thr Ala Ser Val Val Cys Leu
        115                 120                 125

Leu Asn Asn Phe Tyr Pro Arg Glu Ala Lys Val
        130                 135

<210> SEQ ID NO 25
<211> LENGTH: 5
<212> TYPE: PRT
<213> ORGANISM: Homo sapiens
```

```
<400> SEQUENCE: 25

Ser Tyr Thr Met His
1               5

<210> SEQ ID NO 26
<211> LENGTH: 17
<212> TYPE: PRT
<213> ORGANISM: Homo sapiens

<400> SEQUENCE: 26

Phe Ile Ser Tyr Asp Gly Asn Asn Lys Tyr Tyr Ala Asp Ser Val Lys
1               5                   10                  15

Gly

<210> SEQ ID NO 27
<211> LENGTH: 9
<212> TYPE: PRT
<213> ORGANISM: Homo sapiens

<400> SEQUENCE: 27

Thr Gly Trp Leu Gly Pro Phe Asp Tyr
1               5

<210> SEQ ID NO 28
<211> LENGTH: 12
<212> TYPE: PRT
<213> ORGANISM: Homo sapiens

<400> SEQUENCE: 28

Arg Ala Ser Gln Ser Val Gly Ser Ser Tyr Leu Ala
1               5                   10

<210> SEQ ID NO 29
<211> LENGTH: 7
<212> TYPE: PRT
<213> ORGANISM: Homo sapiens

<400> SEQUENCE: 29

Gly Ala Phe Ser Arg Ala Thr
1               5

<210> SEQ ID NO 30
<211> LENGTH: 9
<212> TYPE: PRT
<213> ORGANISM: Homo sapiens

<400> SEQUENCE: 30

Gln Gln Tyr Gly Ser Ser Pro Trp Thr
1               5

<210> SEQ ID NO 31
<211> LENGTH: 118
<212> TYPE: PRT
<213> ORGANISM: Homo sapiens

<400> SEQUENCE: 31

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45
```

```
                                   -continued

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 32
<211> LENGTH: 108
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

CANCER TREATMENT

This application is a national stage application under 35 U.S.C. 0371 of International Patent Application No. PCT/IB2010/054465, filed on Oct. 4, 2010, which claims the benefit of U.S. Provisional Application No. 61/250,711, filed on Oct. 12, 2009. The disclosures of the prior applications are hereby incorporated by reference in their entirety.

FIELD

The present invention relates to methods of treating cancer, such as melanoma, by administering a CTLA4 antagonist to a subject with a serum C-Reactive Protein (CRP) concentration that is less than or equal to a certain pre-determined level. The invention further relates to methods of treating cancer by determining the level of serum CRP concentration in a subject, and then administering a CTLA4 antagonist if the CRP concentration is less than or equal to a certain pre-determined level. The invention further relates to, among other things, the use of serum CRP concentration as a predictive factor of a subject's response to a cancer treatment.

BACKGROUND

One approach to cancer therapy is to target the immune system ("immunotherapy") rather than and/or in addition to targeting the tumor itself. One cancer immunotherapy approach targets cytotoxic T lymphocyte-associated antigen 4 (CTLA4; CD152), which is a cell surface receptor expressed on activated T cells. Binding of CTLA4 to its natural ligands, B7.1 (CD80) and B7.2 (CD86), delivers a negative regulatory signal to T cells, and blocking this negative signal results in enhanced T cell immune function and antitumor activity in animal models (Thompson and Allison *Immunity* 7:445-450 (1997); McCoy and LeGros *Immunol. & Cell Biol.* 77:1-10 (1999)). Several studies have demonstrated that CTLA4 blockade using antibodies markedly enhances T cell-mediated killing of tumors and can induce antitumor immunity (Leach et al., Science 271:1734-1736 (1996); Kwon et al. *Proc. Natl. Acad. Sci. USA* 94:8099-8103 (1997); Kwon et al., *Natl. Acad. Sci. USA* 96:15074-15079 (1999)).

The goal of treatment for metastatic cancer is to prolong survival. There are no approved or experimental agents that have been shown to improve survival in patients with melanoma or to induce tumor response in a large percentage of melanoma patients. In some cases, CTLA4 blocking agents have been shown to induce objective tumor responses in approximately 7-15% of patients with melanoma, but can cause serious side effects. No association of a predictive biomarker for survival benefit for an immunotherapy regimen has been established.

SUMMARY

The present invention as disclosed herein relates to the finding that the serum concentration of acute-phase reactants (such as CRP) is a predictive marker for survival of patients treated with a CTLA4 antagonist.

Accordingly, one aspect of the invention provides a method of treating cancer comprising administering a CTLA4 antagonist to a subject with a serum concentration of at least one acute-phase reactant that is less than or equal to 1.5 times the upper limit of normal as determined by an assay method used to measure the concentration of said acute-phase reactant. In one embodiment, the at least one acute-phase reactant is CRP. In a further embodiment, the at least one acute-phase reactant is IL-6.

In a further aspect, the invention provides a method of treating cancer comprising: a) determining the serum concentration of at least one acute-phase reactant in a subject; and b) administering a CTLA4 antagonist to the subject if the acute-phase reactant concentration in said subject is less than or equal to an amount that is from 1 to 2 times the upper limit of normal as determined by an assay method used to measure the acute-phase reactant concentration. In one embodiment, such amount is 2.0, 1.9, 1.8, 1.7, 1.6, 1.5, 1.4, 1.3, 1.2, 1.1, or 1.0 times the upper limit of normal as determined by an assay method used to measure the acute-phase reactant concentration. In one embodiment, the at least one acute-phase reactant is CRP. In a further embodiment, the at least one acute-phase reactant is IL-6.

In a further aspect, the invention provides a method of predicting the benefit for a cancer patient of an immunotherapy treatment, comprising: a) measuring the serum concentration of at least one acute-phase reactant in the patient; b) comparing said serum concentration to the upper limit of normal for the assay used to measure the concentration of said at least one acute-phase reactant, wherein a serum concentration of the acute-phase reactant in the patient of less than or equal to an amount that is from 1 to 2 times the upper limit of normal as determined by an assay method used to measure the acute-phase reactant concentration. In one embodiment, such amount is 2.0, 1.9, 1.8, 1.7, 1.6, 1.5, 1.4, 1.3, 1.2, 1.1, or 1.0 times the upper limit of normal as determined by an assay method used to measure the acute-phase reactant concentration. In one embodiment, the at least one acute-phase reactant is CRP. In a further embodiment, the at least one acute-phase reactant is IL-6.

In a further aspect, the invention provides a method for predicting the benefit for a cancer patient of an immunotherapy treatment, comprising: a) measuring the serum concentration of at least one acute-phase reactant in the patient; b) comparing said serum concentration to the upper limit of normal for the assay used to measure the concentration of said acute-phase reactant, wherein a serum concentration in the patient of less than or equal to 2.0, 1.9, 1.8, 1.7, 1.6, 1.5, 1.4, 1.3, 1.2, 1.1, or 1.0 times the upper limit of normal is indicative of a higher likelihood of achieving a benefit from the immunotherapy treatment as compared to a cancer patient with a serum concentration that is more than 2.0, 1.9, 1.8, 1.7, 1.6, 1.5, 1.4, 1.3, 1.2, 1.1, or 1.0 times the upper limit of normal. In one embodiment, the at least one acute-phase reactant is CRP. In a further embodiment, the at least one acute-phase reactant is IL-6.

In a further aspect, the invention provides any of the methods described herein, wherein said cancer is melanoma. In a further aspect, said melanoma is chosen from stage 0 melanoma (melanoma in situ), stage I/II melanoma (invasive melanoma), stage II melanoma (high risk melanoma), stage III melanoma (regional metastasis), and stage IV melanoma (distant metastasis).

In a further aspect, the invention provides any of the methods described herein, wherein the immunotherapy treatment comprises administering a CTLA4 antagonist to the cancer patient.

In a further aspect, the invention provides any of the methods described herein, wherein said CTLA4 antagonist is an anti-CTLA4 antibody or antigen-binding portion thereof. In a further aspect, said anti-CTLA4 antibody or antigen-binding portion thereof comprises at least one CDR amino acid sequence selected from SEQ ID NOs:1 to 6, 9 to 14, 17 to 22, and 25 to 30. In a further aspect, said anti-CTLA4 antibody or antigen-binding portion thereof comprises a $V_H$ chain amino acid sequence as set forth in SEQ ID NOs: 7, 15, 23, or 31. In a further aspect, said anti-CTLA4 antibody or antigen-binding portion thereof comprises a $V_L$ chain amino acid sequence as set forth in SEQ ID NOs: 8, 16, 24, or 32. In a further aspect, said anti-CTLA4 antibody or antigen-binding portion thereof comprises a $V_H$ chain amino acid sequence as set forth in SEQ ID NO:23 and a $V_L$ chain amino acid sequence as set forth in SEQ ID NO:24. In a further aspect, said anti-CTLA4 antibody or antigen-binding portion thereof comprises a $V_H$ chain amino acid sequence as set forth in SEQ ID NO:31 and a $V_L$ chain amino acid sequence as set forth in SEQ ID NO:32. In a further aspect, said antibody is tremelimumab, or an antigen-binding portion thereof. In a further aspect, said antibody is ipilimumab, or an antigen-binding portion thereof.

In a further aspect, the invention provides any of the methods described herein, wherein the benefit from the immunotherapy in a cancer patient with a serum CRP concentration of less than or equal to 2.0, 1.9, 1.8, 1.7, 1.6, 1.5, 1.4, 1.3, 1.2, 1.1, or 1.0 times the upper limit of normal is an improvement in overall survival as compared to a cancer patient with a serum CRP concentration of more than 2.0, 1.9, 1.8, 1.7, 1.6, 1.5, 1.4, 1.3, 1.2, 1.1, or 1.0 times the upper limit of normal.

In a further aspect, the invention provides the use of CRP serum concentration as a predictive factor of a cancer patient's response to therapy comprising a CTLA4 antagonist. In one aspect, said CTLA4 antagonist is an anti-CTLA4 antibody or antigen-binding portion thereof. In a further aspect, said anti-CTLA4 antibody or antigen-binding portion thereof comprises at least one CDR amino acid sequence selected from SEQ ID NOs:1 to 6, 9 to 14, 17 to 22, and 25 to 30. In a further aspect, said anti-CTLA4 antibody or antigen-binding portion thereof comprises a $V_H$ chain amino acid sequence as set forth in SEQ ID NOs: 7, 15, 23, or 31. In a further aspect, said anti-CTLA4 antibody or antigen-binding portion thereof comprises a $V_L$ chain amino acid sequence as set forth in SEQ ID NOs: 8, 16, 24, or 32. In a further aspect, said anti-CTLA4 antibody or antigen-binding portion thereof comprises a $V_H$ chain amino acid sequence as set forth in SEQ ID NO:23 and a $V_L$ chain amino acid sequence as set forth in SEQ ID NO:24. In a further aspect, said anti-CTLA4 antibody or antigen-binding portion thereof comprises a $V_H$ chain amino acid sequence as set forth in SEQ ID NO:31 and a $V_L$ chain amino acid sequence as set forth in SEQ ID NO:32. In a further aspect, said antibody is tremelimumab, or an antigen-binding portion thereof. In a further aspect, said antibody is ipilimumab, or an antigen-binding portion thereof.

In a further aspect, the invention provides any of the methods described herein, wherein said CTLA4 antagonist is administered in combination with an IL-6 antagonist (i.e. an agent that results in IL-6 blockade). In some embodiments, said IL-6 antagonist is administered prior to the CTLA4 antagonist. In some embodiments, the IL-6 antagonist is administered, and then a CTLA4 antagonist is administered if the serum CRP concentration is determined to be less than an amount that is from 1 to 2 times the upper limit of normal as determined by an assay method used to measure the serum CRP concentration. In one embodiment, such amount is 2.0, 1.9, 1.8, 1.7, 1.6, 1.5, 1.4, 1.3, 1.2, 1.1, or 1.0 times the upper limit of normal as determined by an assay method used to measure the serum CRP concentration. In one embodiment, said IL-6 antagonist is an anti-IL-6 antibody, or antigen-binding portion thereof. In another embodiment, said IL-6 antagonist is an anti-IL-6 receptor antibody or antigen-binding portion thereof.

In a further aspect, the invention provides any of the methods and uses as described herein, where the CRP level is measured and compared to the upper limit of normal no more than 7 days, no more than 6 days, no more than 5 days, no more than 4 days, no more than 3 days, no more than 2 days, or no more than 1 day prior to administering a CTLA4 antagonist. The present invention further provides any of the methods and uses as described herein, where a baseline CRP level is determined and compared to the upper limit of normal no more than 4 weeks, no more than 3 weeks, no more than 2 weeks, or no more than 1 week prior to the potential CTLA4 antagonist therapy. Such a baseline determination can be measured by obtaining at least 2, at least 3, at least 4, or at least 5 or more CRP level samples at different time points during the baseline determination prior to the potential CTLA4 antagonist therapy. In one aspect, once a baseline CRP level is determined, the CRP level is then measured and compared to the upper limit of normal no more than 7 days, no more than 6 days, no more than 5 days, no more than 4 days, no more than 3 days, no more than 2 days, or no more than 1 day prior to administering a CTLA4 antagonist.

BRIEF DESCRIPTION OF THE DRAWINGS

The foregoing summary, as well as the following detailed description of the invention, will be better understood when read in conjunction with the appended drawings. In the drawings.

DETAILED DESCRIPTION

Figure 1:
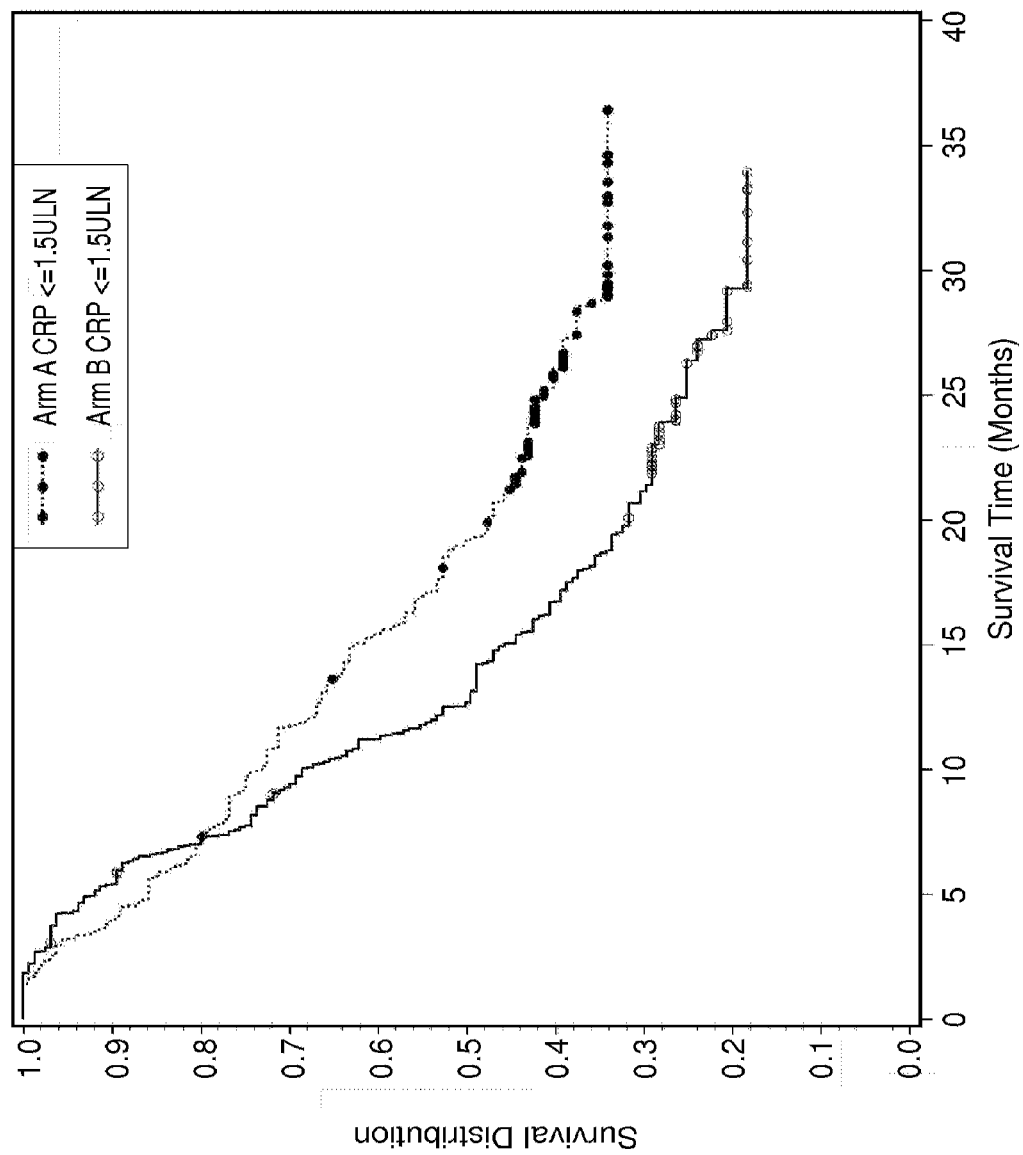
FIG. 1 shows a Kaplan Meier plot of overall survival from study A3671009 where the CRP level is <=1.5 times the ULN in both treatment arms A and B.

The present invention relates generally to the identification of a biological marker of patients who can benefit from treatment with CTLA4 blockade. More specifically, the present invention relates to the discovery that serum C-reactive protein (CRP) data can be used in the selection of patients for treatment with CTLA4 blockade. This discovery is surprising because it goes against traditional thinking in the field of cancer immunotherapy, which generally assumes that inflammation in a tumor is actually required for induction of an effective immune response against the tumor.

In order that the present disclosure may be more readily understood, certain terms are first defined. Additional definitions are set forth throughout the detailed description.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The methods and techniques of the present disclosure are generally performed according to methods well known in the art and as described in various general and more specific references that are cited and discussed throughout the present specification unless otherwise indicated. Such references include, e.g., Sambrook and Russell, *Molecular Cloning, A Laboratory Approach*, Cold Spring Harbor Press, Cold Spring Harbor, N.Y. (2001), Ausubel et al., *Current Protocols in Molecular Biology*, John Wiley & Sons, NY (2002), and Harlow and Lane *Antibodies: A Laboratory Manual*, Cold Spring Harbor Laboratory Press, Cold Spring Harbor, N.Y. (1990). Enzymatic reactions and purification techniques are performed according to manufacturer's specifications, as commonly accomplished in the art or as described herein.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "upper limit of normal", or "ULN", as used herein, refers to a reference value that is determined by, and associated with, a particular assay method used to measure a particular property. For example, consider a given diagnostic assay method used to measure the level of a certain substance in a subject. When this assay is used to measure the substance level in a group of "normal", healthy subjects, the test results will typically provide a Gaussian distribution, with most results located around an average (or "mean") and with decreasing numbers of subjects having results farther away from the mean result. In a representative population of typical, healthy people, about two thirds will have results within one standard deviation of the mean, and 95.5% of results are within two standard deviations. Thus 2.25% of healthy individuals have a test result more than two standard deviations above the mean. Similarly, 2.25% of results are more than two standard deviations below the mean. When an upper limit of normal is chosen for most laboratory tests, it is generally set at the level of two standard deviations above the mean. Accordingly, with reference to the ULN for serum CRP concentration, such ULN will be a concentration value that is set by the assay method (e.g. as determined by the laboratory that administers the assay) that is used to measure the serum CRP concentration. Accordingly, such ULN values may vary from assay to assay, but will be readily available based on the assay method that is chosen.

The term "serum CRP concentration", as used herein, refers to the concentration of CRP in a subject's blood serum as measured by any appropriate assay by drawing blood serum and carrying out the assay according to the assay protocol. In some cases, such concentration will be a baseline concentration, wherein the result of a CRP assay is performed on serum drawn from the subject not more than 14 days prior to the first dose of a CTLA4 antagonist. For example, in one embodiment, the serum CRP concentration is determined one day prior to treatment, 2 days prior to treatment, three days prior to treatment, four days prior to treatment, five days prior to treatment, six days prior to treatment, or seven days prior to treatment.

As will be appreciated by those of skill in the art, as used herein, the term "acute-phase reactant" refers to substances that are produced by the liver in response to a change in plasma concentration of acute-phase proteins. Acute-phase proteins are a class of proteins whose plasma concentrations increase (positive acute-phase proteins) or decrease (negative acute-phase proteins) in response to inflammation. This response is called the acute-phase reaction (also known as the acute-phase response). In response to injury, local inflammatory cells (neutrophil granulocytes and macrophages) secrete a number of cytokines into the bloodstream, most notably interleukins such as IL-1, IL-6, and IL-8, and TNF-α. The liver responds by producing a large number of acute-phase reactants (e.g. CRP).

Except where noted, the terms "patient" and "subject" are used interchangeably and refer to mammals such as human patients and non-human primates, as well as veterinary subjects such as rabbits, rats, and mice, and other animals.

As used herein, the term "treat", "treating", or "treatment" means reducing the frequency with which symptoms of a disease (i.e., tumor growth and/or metastasis, or other effect mediated by the numbers and/or activity of immune cells, and the like) are experienced by a subject. The term includes the administration of the compounds or agents disclosed herein to prevent or delay the onset of the symptoms, complications, or biochemical indicia of a disease (e.g., melanoma), and/or alleviating the symptoms, arresting, and/or inhibiting further development of the disease, condition, or disorder, and/or prolonging survival of the subject suffering from the disease. Treatment may be prophylactic (to prevent or delay the onset of the disease, or to prevent the manifestation of clinical or subclinical symptoms thereof) or therapeutic suppression or alleviation of symptoms after the manifestation of the disease.

As used herein, the term "CTLA4 antagonist" refers to any agent that can interfere with the specific interaction of a CTLA4 receptor with its natural ligands B7.1 and B7.2. An antagonist can act as a competitive inhibitor or a noncompetitive inhibitor of CTLA4 binding to its ligands. Such agents can include antibodies (including antigen binding portions thereof), peptides, and non-peptide small organic molecules, as well as substances (such as anti-sense or interfering RNA molecules) that decrease the expression of a CTLA4 receptor. An anti-CTLA4 antibody (or antigen binding portion thereof) that can interfere with the binding of CTLA4 to its ligands B7.1 and/or B7.2 is one example of a CTLA4 antagonist. Other antagonists are described herein, and/or will be readily apparent to those of skill in the art.

As used herein, the twenty conventional amino acids and their abbreviations follow conventional usage. See *Immunology—A Synthesis* (2nd Edition, E. S. Golub and D. R. Gren, Eds., Sinauer Associates, Sunderland, Mass. (1991)).

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). The CDR regions can be determined using the Kabat or Chothia numbering systems, both of which are well known to those of skill in the art. See, e.g. Kabat, E. A., et al. (1991) Sequences of Proteins of Immunological Interest, Fifth Edition, U.S. Department of Health and Human Services, NIH Publication No. 91-3242; Chothia and Lesk, *J. Mol. Biol.* 196:901-917 (1987). Each $V_H$ and $V_L$ is composed of three CDRs and four FRs, arranged from amino-terminus to carboxy-terminus in the following order: FR1, CDR1, FR2, CDR2, FR3, CDR3, FR4. Throughout the present disclosure, the three CDRs of the heavy chain are referred to as H-CDR1, H-CDR2, and H-CDR3. Similarly, the three CDRs of the light chain are referred to as L-CDR1, L-CDR2, and L-CDR3. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Within light and heavy chains, the variable and constant regions are joined by a "J" region of about 12 or more amino acids, with the heavy chain also including a "D" region of about 10 or more amino acids. See generally, Fundamental Immunology Ch. 7 (Paul, W., ed., $2^{nd}$ ed. Raven Press, N.Y. (1989)).

A "human" antibody, or antigen-binding portion thereof, is hereby defined as one that is not chimeric (e.g., not "humanized") and not from (either in whole or in part) a non-human species. A human antibody or antigen-binding portion can be derived from a human or can be a synthetic human antibody. A "synthetic human antibody" is defined herein as an antibody having a sequence derived, in whole or in part, in silico from synthetic sequences that are based on the analysis of known human antibody sequences. In silico design of a human antibody sequence or fragment thereof can be achieved, for example, by analyzing a database of human antibody or antibody fragment sequences and devising a polypeptide sequence utilizing the data obtained therefrom. Another example of a human antibody or antigen-binding portion, is one that is encoded by a nucleic acid isolated from a library of antibody sequences of human origin (i.e., such library being based on antibodies taken from a human natural source).

A "humanized antibody", or antigen-binding portion thereof, is defined herein as one that is (i) derived from a non-human source (e.g., a transgenic mouse which bears a heterologous immune system), which antibody is based on a human germline sequence; or (ii) chimeric, wherein the variable domain is derived from a non-human origin and the constant domain is derived from a human origin or (iii) CDR-grafted, wherein the CDRs of the variable domain are from a non-human origin, while one or more frameworks of the variable domain are of human origin and the constant domain (if any) is of human origin. In the case where the CDRs are grafted from a non-human origin, said CDRs can be subsequently altered in order to improve the binding affinity to the target of interest.

The term "antigen-binding portion" of an antibody (or simply "antibody portion"), as used herein, refers to one or more fragments of an antibody that retain the ability to specifically bind to an antigen (e.g., CTLA4). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., Nature 341:544-546 (1989)), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). Such single chain antibodies are also intended to be encompassed within the term "antigen-binding portion" of an antibody. These antibody fragments may be obtained using any suitable technique, including conventional techniques known to those with skill in the art, and the fragments may be screened for utility in the same manner as are intact antibodies.

Also, as used herein, an "immunoglobulin" (Ig) is defined as a protein belonging to the class, or isotype, IgG, IgM, IgE, IgA, or IgD (or any subclass thereof), and includes all conventionally known antibodies and antigen-binding portions thereof.

As used herein, "sequence identity" between two polypeptide sequences indicates the percentage of amino acids that are identical between the sequences. The amino acid sequence identity of polypeptides can be determined conventionally using known computer programs such as Bestfit, FASTA, or BLAST (see, e.g. Pearson, Methods Enzymol. 183:63-98 (1990); Pearson, Methods Mol. Biol. 132:185-219 (2000); Altschul et al., J. Mol. Biol. 215:403-410 (1990); Altschul et al., Nucelic Acids Res. 25:3389-3402 (1997)). When using Bestfit or any other sequence alignment program to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, fragments, or variants thereof disclosed herein.

As used herein, "isotype" or "class" refers to the antibody class (e.g., IgM or IgG) that is encoded by the heavy chain constant region genes. The constant domains of antibodies are not involved in binding to antigen, but exhibit various effector functions. Depending on the amino acid sequence of the heavy chain constant region, a given human antibody or immunoglobulin can be assigned to one of five major classes of immunoglobulins: IgA, IgD, IgE, IgG, and IgM. The structures and three-dimensional configurations of different classes of immunoglobulins are well-known. Of the various human immunoglobulin classes, only human IgG1, IgG2, IgG3, IgG4, and IgM are known to activate complement. Human IgG1 and IgG3 are known to mediate ADCC in humans.

As used herein, "subclass" refers to the further specification within an isotype of the heavy chain constant region gene, such as, for example, the IgG1, IgG2, IgG3, or IgG4 subclasses within the IgG isotype.

As used herein, the term "interfere," when used in reference to the action of an agent antagonist on the specific interaction of a receptor and its ligand, means that the affinity of the interaction is decreased below the level of binding that occurs in the absence of the agent. The skilled artisan will recognize that the association of a receptor and its ligand is a dynamic relationship that occurs among a population of such molecules such that, at any particular time, a certain proportion of receptors and ligands will be in association. An agent that interferes with the specific interaction of a receptor and its ligand, therefore, reduces the relative number of such interactions occurring at a given time and, in some cases, can completely inhibit all such associations.

C-reactive protein (CRP), also known as PTX1, MGC88244, or MGC149895, is a member of the pentraxin family of proteins and is synthesized by the liver in response to most forms of inflammation, infection, tissue damage and malignancies. CRP is a member of the class of acute-phase reactants as its levels rise dramatically during inflammatory processes occurring in the body. Its production is controlled mainly by IL-6, which is produced predominantly by macrophages as well as adipocytes. Accordingly, IL-6 blockade is expected to result in decreased levels of CRP. For example, treatment with the IL-6 receptor inhibitor tocilizumab was noted to reduce CRP levels (see package insert for ACTEMRA® (tocilizumab), Section 12.2). A similar finding was observed for ALD518, a humanized anti-IL-6 antibody (see Clarke, S. J. et al, *J. Clin. Oncol.* 27:15s (2009) (suppl; abstr 3025)). Thus, in one aspect of the present invention, an IL-6 antagonist (for example an agent that results in IL-6 blockade, such as an IL-6 or IL-6 receptor inhibitor) can be administered first as a means to reduce CRP levels, which can then be followed by administering a CTLA4 antagonist according to the present invention. Examples of such IL-6 antagonists include anti-IL-6 receptor antibodies, such as tocilizumab, and anti-IL-6 antibodies, such as ALD518. Other IL-6 antagonists that can be used within the scope of the present invention will be readily recognized by those of skill in the art. CRP is also thought to assist in complement binding to foreign and damaged cells and enhances phagocytosis by macrophages, which express a receptor for CRP (Pepys et al., *J. Clin. Invest.* 111(12):1805-1812 (2003)).

Following an acute-phase stimulus, CRP values may increase from up to 10,000-fold as compared to a level prior to the acute-phase stimulus. Plasma CRP is produced only by hepatocytes, predominantly under transcriptional control by the cytokine IL-6, although other sites of local CRP synthesis and possibly secretion have been suggested. De novo hepatic synthesis starts very rapidly after a single stimulus, serum concentrations rising above 5 mg/L by about 6 hours and peaking around 48 hours (Pepys et al., J. Clin. Invest. 111 (12): 1805-1812 (2003)).

It has been previously shown that in cancer patients, IL-6 may be produced by host cells, such as leukocytes, or by cancer cells. Also, the role of elevated serum CRP as a prognostic factor for poor survival has been established for patients with melanoma (Deichmann et al., British Journal of Cancer 91:699-702 (2004); Findeisen et al., J. Clin. Oncol. 13:2199-2208 (2009) and other types of tumors (Blay et al., Cancer Res 52:3317-3322 (1992); Moses et al., Oncology Reports 21:1091-1095 (2009); Falconer et al., Cancer 75:2077-2082 ((1995); Gough et al., Clin Exp Immunol 105: 529-536 (1996)). However, serum CRP has never previously been shown to predict survival benefit from a specific treatment.

The serum concentration of acute phase reactants, such as CRP, in a subject can be determined using various analytical assay methods that are well known in the art, including ELISA, immunoturbidimetry, rapid immunodiffusion, and visual agglutination. For example, assays that are known include those described in Erlandsen et al. *Scand. J. Clin. Lab Invest.* 60:37-43 (2000). It is typical for each assay to have an "upper limit of normal" (ULN) value associated with the specific assay method. Such ULN is typically determined from a sufficient sample size of normal, healthy subjects using the particular assay method to measure the serum CRP concentration. The ULN is then typically determined to be the highest measured CRP serum concentration that is still considered within the normal range (e.g. within two standard deviations of the mean). Since such ULN values will vary depending on the particular assay method employed to measure serum CRP concentration, each specific assay will have a unique ULN value that is associated with that assay method. Accordingly, since the methods described herein are intended to be carried out using any possible method of measuring serum CRP concentration, the ULN that is referenced as part of the invention disclosed herein is the ULN that is associated with whatever assay method is used to measure the serum CRP concentration.

As shown herein, CRP serum concentrations can be used to predict whether a cancer patient will be likely to benefit from an immunotherapy treatment compared to chemotherapy. As described further in the Examples, the invention has been demonstrated herein using studies in which patients with previously-untreated, unresectable stage IV melanoma were examined for their serum concentrations of CRP. Patients who had low levels of CRP serum concentrations had better outcomes if they were treated with immunotherapy than if they were treated with chemotherapy. Patients who had high levels of CRP serum concentrations did not have better outcomes if they were treated with immunotherapy than if they were treated with chemotherapy. Overall response rate appeared to be influenced by baseline CRP serum concentrations for patients treated with immunotherapy treatment. In addition, for all patients with low CRP serum concentrations, those receiving immunotherapy had a higher response rate than those receiving chemotherapy.

Accordingly, one aspect of the present invention provides a method for predicting the benefit for a cancer patient of an immunotherapy treatment, comprising the step of measuring the serum concentration of CRP of a patient prior to or on the same day of receiving the first dose of the immunotherapy treatment and comparing said CRP serum concentration to the upper limit of normal. If the serum concentration of CRP of the patient is less than or equal to a certain threshold level (e.g. in relation to the ULN), then the patient is expected to benefit from the immunotherapy treatment as compared to chemotherapy treatment. Also, if the serum concentration of CRP of the patient is less than or equal to a certain threshold level, an improvement in the overall response rate to the immunotherapy treatment is expected as compared to the overall response rate of a cancer patient with a serum concentration of CRP of more than a threshold level of CRP serum concentration.

In particular, the methods described herein can be used to predict whether a patient will have improved survival associated with the immunotherapy treatment, or will have an increased likelihood of response to the immunotherapy treatment as compared to a patient with a lower serum concentration of CRP. As also shown herein, the methods of the invention are of particular interest to a patient with melanoma.

Anti-CTLA4 Antibodies

As shown in the Examples, the methods of the invention can be used in an immunotherapy treatment using an anti-CTLA4 monoclonal antibody such as tremelimumab. Tremelimumab, as well as other antibodies such as ipilimumab, that can be used in the present invention, and methods of producing them, are described in U.S. Pat. Nos. 6,682,736 and 6,984,720. Such antibodies include, but are not limited to, antibodies that are designated in these references as antibodies 3.1.1, 4.1.1, 4.8.1, 4.10.2, 4.13.1, 4.14.3, 6.1.1, 11.2.1 (also known as tremelimumab, or ticilimumab), 11.6.1, 11.7.1, 12.3.1.1, and 12.9.1.1, as well as ipilimumab (also known as 10D1 or MDX-010).

The amino and nucleic acid sequences of such antibodies as set forth in U.S. Pat. Nos. 6,682,736 and 6,984,720 are incorporated by reference herein in their entirety. Briefly, antibodies that can be used in the present invention include antibodies having amino acid sequences of the heavy and light chains of an antibody such as, but not limited to, antibody 3.1.1, 4.1.1, 4.8.1, 4.10.2, 4.13.1, 4.14.3, 6.1.1, 11.2.1

(tremelimumab), 11.6.1, 11.7.1, 12.3.1.1, 12.9.1.1, and 10D1 (ipilimumab). The invention also contemplates the use of antibodies, or antigen-binding portions thereof, having the amino acid sequences of the CDRs of the heavy and light chains of these antibodies, as well as those having changes in the CDR regions, as described in the above-cited patents. The invention also contemplates the use of antibodies having the variable regions of the heavy and light chains of those antibodies. In another embodiment, the antibody is selected from an antibody having the full length, variable region, or CDR, amino acid sequences of the heavy and light chains of antibodies selected from 3.1.1, 4.1.1, 4.8.1, 4.10.2, 4.13.1, 4.14.3, 6.1.1, 11.2.1 (tremelimumab), 11.6.1, 11.7.1, 12.3.1.1, 12.9.1.1, and 10D1 (ipilimumab) as described in U.S. Pat. Nos. 6,682,736 and 6,984,720.

In another embodiment, the amino acid sequence of the $V_H$ comprises an amino acid sequence as set forth in SEQ ID NO:7, 15, 23, or 31. In yet another embodiment, the $V_L$ comprises an amino acid sequences as set forth in SEQ ID NO:8, 16, 24, or 32. More preferably, the $V_H$ and $V_L$ comprise the amino acid sequences set forth in SEQ ID NO:7 ($V_H$ 4.1.1) and SEQ ID NO:8 ($V_L$ 4.1.1), respectively; the amino acid sequences set forth in SEQ ID NO:15 ($V_H$ 4.13.1) and SEQ ID NO:16 ($V_L$ 4.13.1), respectively; the amino acid sequences set forth in SEQ ID NO:23 ($V_H$ 11.2.1) and SEQ ID NO:24 ($V_L$ 11.2.1), respectively; or the amino acid sequences set forth in SEQ ID NO:31 ($V_H$ 10D1) and SEQ ID NO:32 ($V_L$ 10D1), respectively.

Furthermore, the antibody can comprise a heavy chain amino acid sequence comprising human CDR amino acid sequences derived from the $V_H$ 3-30 or 3-33 gene, or conservative substitutions or somatic mutations therein. The antibody can also comprise CDR regions in its light chain derived from the A27 or O12 gene, i.e., fewer than five, or fewer than ten such mutations. The antibody can also comprise framework regions from those genes, including those that differ by fewer than five, or fewer than ten amino acids. Also included are antibodies with framework regions described herein that have been mutated to reflect the original germ-line sequence.

In other embodiments of the invention, the antibody inhibits binding between CTLA4 and B7.1, B7.2, or both. For example, the antibody can inhibit binding with B7.1 with an $IC_{50}$ of about 100 nM or lower, such as about 10 nM or lower, for example about 5 nM or lower, such as about 2 nM or lower, or even further, for example, about 1 nM or lower. Likewise, the antibody can inhibit binding with B7.2 with an $IC_{50}$ of about 100 nM or lower, for example, 10 nM or lower, further for example about 5 nM or lower, yet further for example, about 2 nM or lower, or even further, for example, about 1 nM or lower.

Further, in another embodiment, the anti-CTLA4 antibody or antigen-binding portion thereof has a binding affinity for CTLA4 of about $10^{-8}$, or greater affinity, such as about $10^{-9}$ or greater affinity, for example about $10^{-19}$ or greater affinity, and even further, for example, about $10^{-11}$ or greater affinity.

The anti-CTLA4 antibody or antigen-binding portion can compete for binding with an antibody having heavy and light chain amino acid sequences of an antibody selected from antibodies 4.1.1, 11.2.1, 4.13.1 and 10D1.

In another embodiment, the antibody can cross-compete with an antibody having a heavy and light chain sequence, a variable heavy and a variable light chain sequence, and/or the heavy and light CDR sequences of antibody 4.1.1, 4.13.1, 11.2.1 or 10D1. For example, the antibody can bind to the epitope to which an antibody that has heavy and light chain amino acid sequences, variable sequences and/or CDR sequences, of an antibody chosen from 4.1.1, 4.13.1, 11.2.1, and 10D1 binds.

In another embodiment, the invention is practiced using an anti-CTLA4 antibody, or antigen-binding portion thereof, that comprises the H-CDR1, H-CDR2, and H-CDR3, and L-CDR1, L-CDR2, and L-CDR3, of an antibody selected from 4.1.1, 4.13.1, 11.2.1, and 10D1, or sequences having changes from said CDR sequences selected from the group consisting of conservative changes, wherein the conservative changes are selected from the group consisting of replacement of nonpolar residues by other nonpolar residues, replacement of polar charged residues by other polar uncharged residues, replacement of polar charged residues by other polar charged residues, and substitution of structurally similar residues; non-conservative substitutions, wherein the non-conservative substitutions are selected from the group consisting of substitution of polar charged residues for polar uncharged residues and substitution of nonpolar residues for polar residues, additions and deletions.

In a further embodiment of the invention, the antibody or antigen-binding portion thereof contains fewer than 10, 7, 5, or 3 amino acid changes from the germline sequence in the framework or CDR regions. In another embodiment, the antibody contains fewer than 5 amino acid changes in the framework regions and fewer than 10 changes in the CDR regions. In one embodiment, the antibody contains fewer than 3 amino acid changes in the framework regions and fewer than 7 changes in the CDR regions. In a one embodiment, the changes in the framework regions are conservative and those in the CDR regions are somatic mutations.

In another embodiment, the antibody has at least 80%, at least 85%, at least 90%, at least 95%, or at least 99%, sequence identity over the heavy and light chain CDR1, CDR2 and CDR3 sequences with the CDR sequences of an antibody selected from 4.1.1, 4.13.1, 11.2.1, and 10D1. In one embodiment, the antibody shares 100% sequence identity over the heavy and light chain CDR1, CDR2 and CDR3 regions with the corresponding sequence of antibody 4.1.1, 4.13.1, 11.2.1, or 10D1.

In yet another embodiment, the antibody has at least 80%, at least 85%, at least 90%, at least 95%, or at least 99%, sequence identity over the heavy and light chain variable region sequences with the corresponding variable region sequences of antibody 4.1.1, 4.13.1, 11.2.1, or 10D1. In one embodiment, the antibody shares 100% sequence identity over the heavy and light chain variable region sequences with the corresponding sequences of antibody 4.1.1, 4.13.1, 11.2.1, or 10D1.

While various anti-CTLA4 antibodies and antigen-binding portions have been described herein, the skilled artisan, based upon the disclosure provided herein, would appreciate that the invention encompasses a wide variety of anti-CTLA4 antibodies and antigen-binding portions and is not limited to those that have been explicitly disclosed. More particularly, while human antibodies have been described, the invention is in no way limited to human antibodies; rather, the invention encompasses useful antibodies regardless of species origin, and includes, among others, chimeric humanized and/or primatized antibodies. Also, although the antibodies exemplified herein were obtained using a transgenic mammal, e.g., a mouse comprising a human immune repertoire, the skilled artisan, based upon the disclosure provided herein, would understand that the present invention is not limited to an antibody produced by this or by any other particular method. Instead, the invention includes an anti-CTLA4 antibody or antigen-binding portion produced by any method, including, but not limited to, a method known in the art (e.g., screening phage display libraries, and the like) or to be developed in the future for producing an anti-CTLA4 antibody. Based upon the extensive disclosure provided herein and in, e.g., U.S. Pat. Nos. 6,682,736 and 6,984,720, one skilled in the art can readily produce and identify CTLA4 antagonists that can be used within the scope of the present invention.

The present invention encompasses human antibodies produced using a transgenic non-human mammal, such as the XenoMouse™ (Abgenix, Inc., Fremont, Calif.) as disclosed in U.S. Pat. No. 6,682,736, or the "HuMAb-Mouse™" (Medarex, Princeton, N.J.), which contain human immunoglobulin gene miniloci that encode unrearranged human heavy (mu and gamma) and kappa light chain immunoglobulin sequences, together with targeted mutations that inactivate the endogenous mu and kappa chain loci (Lonberg et al. Nature 368:856-859 (1994), and U.S. Pat. No. 5,770,429).

However, the invention contemplates using human anti-CTLA4 antibodies or antigen-binding portions produced using any transgenic mammal such as, but not limited to, the Kirin TC Mouse™ (Kirin Beer Kabushiki Kaisha, Tokyo, Japan) as described in, e.g., Tomizuka et al., *Proc Natl Acad Sci USA* 97:722 (2000); Kuroiwa et al., *Nature Biotechnol* 18:1086 (2000); U.S. Patent Application Publication No. 2004/0120948, to Mikayama et al.; and the HuMAb-Mouse™ (Medarex, Princeton, N.J.) and XenoMouse™ (Abgenix, Inc., Fremont, Calif.), supra. Thus, the invention encompasses using an anti-CTLA4 antibody or antigen-binding portion produced using any transgenic or other non-human animal.

Moreover, the present invention encompasses using any method for production of a human, or any other antibody specific for CTLA4 produced according to any method known in the art or to be developed in the future for production of antibodies or antigen-binding portions that specifically bind an antigen of interest.

Human antibodies can be developed by methods that include, but are not limited to, use of phage display antibody libraries. Using these techniques, antibodies can be generated to CTLA4 expressing cells, CTLA4 itself, forms of CTLA4, epitopes or peptides thereof, and expression libraries thereto (see e.g. U.S. Pat. No. 5,703,057), which can thereafter be screened for the activities described above.

In another embodiment, the antibodies or antigen-binding portions employed in methods of the invention are not fully human, but "humanized". In particular, murine antibodies or antibodies from other species can be "humanized" or "primatized" using techniques well known in the art. See, e.g., Winter and Harris *Immunol. Today* 14:43-46 (1993), Wright et al. *Crit. Reviews in Immunol.* 12:125-168 (1992), and U.S. Pat. No. 4,816,567, and Mage and Lamoyi in *Monoclonal Antibody Production Techniques and Applications* pp. 79-97, Marcel Dekker, Inc., New York, N.Y. (1987).

As will be appreciated based upon the disclosure provided herein, antibodies or antigen-binding portions for use in the invention can be obtained from a transgenic non-human mammal, and hybridomas derived therefrom, but can also be expressed in cell lines other than hybridomas.

Mammalian cell lines available as hosts for expression are well known in the art and include many immortalized cell lines available from the American Type Culture Collection (ATCC), including but not limited to Chinese hamster ovary (CHO) cells, NS0 (also referred to as NS0), HeLa cells, baby hamster kidney (BHK) cells, monkey kidney cells (COS), and human hepatocellular carcinoma cells (e.g., Hep G2). Non-mammalian prokaryotic and eukaryotic cells can also be employed, including bacterial, yeast, insect, and plant cells.

Various expression systems that are well known in the art can be used, such as, but not limited to, those described in e.g., Sambrook and Russell, *Molecular Cloning, A Laboratory Approach*, Cold Spring Harbor Press, Cold Spring Harbor, N.Y. (2001), and Ausubel et al., *Current Protocols in Molecular Biology*, John Wiley & Sons, NY (2002). These expression systems include dihydrofolate reductase (DHFR)-based systems, among many others. The glutamine synthetase system of expression is discussed in whole or part in connection with European Patents Nos. EP 216 846, EP 256 055, and EP 323 997 and European Patent Application 89303964. In one embodiment, the antibody used is made in NS0 cells using a glutamine synthetase system (GS-NS0). In another embodiment, the antibody is made in CHO cells using a DHFR system. Both systems are well-known in the art and are described in, among others, Barnes et al. *Biotech & Bioengineering* 73:261-270 (2001), and references cited therein.

Site directed mutagenesis of the antibody CH2 domain to eliminate glycosylation may be preferred in order to prevent changes in either the immunogenicity, pharmacokinetic, and/or effector functions resulting from non-human glycosylation. Further, the antibody can be deglycosylated by enzymatic reactions (see, e.g., Thotakura et al. *Meth. Enzymol.* 138:350 (1987)) and/or chemical methods (see, e.g., Hakimuddin et al., *Arch. Biochem. Biophys.* 259:52 (1987)).

Further, the invention encompasses using an anti-CTLA4 antibody comprising an altered glycosylation pattern. The skilled artisan would appreciate, based upon the disclosure provided herein, that an anti-CTLA4 antibody can be modified to comprise additional, fewer, or different glycosylation sites compared with the naturally-occurring antibody. Such modifications are described in, e.g., U.S. Patent Application Publication Nos. 2003/0207336, and 2003/0157108, and International Patent Publication Nos. WO 01/81405 and 00/24893.

Additionally, the invention comprises using an anti-CTLA4 antibody regardless of the glycoform, if any, present on the antibody. Moreover, methods for extensively remodeling the glycoform present on a glycoprotein are well-known in the art and include, e.g., those described in International Patent Publication Nos. WO 03/031464, WO 98/58964, and WO 99/22764, and U.S. Patent Application Publication Nos. 2004/0063911, 2004/0132640, 2004/0142856, 2004/0072290, and U.S. Pat. No. 6,602,684.

Further, the invention encompasses using an anti-CTLA4 antibody with any art-known covalent and non-covalent modification, including, but not limited to, linking the polypeptide to one of a variety of nonproteinaceous polymers, e.g., polyethylene glycol, polypropylene glycol, or polyoxyalkylenes, in the manner set forth in, for example, U.S. Patent Application Publication Nos. 2003/0207346 and 2004/0132640, and U.S. Pat. Nos. 4,640,835; 4,496,689; 4,301,144; 4,670,417; 4,791,192; 4,179,337.

Additionally, the invention encompasses using an anti-CTLA4 antibody, or antigen-binding portion thereof, chimeric protein comprising, e.g., a human serum albumin polypeptide, or fragment thereof. Whether the chimeric protein is produced using recombinant methods by, e.g., cloning of a chimeric nucleic acid encoding the chimeric protein, or by chemical linkage of the two peptide portions, the skilled artisan will understand that such chimeric proteins are well-known in the art and can confer desirable biological properties such as, but not limited to, increased stability and serum half-life to the antibody of the invention and such molecules are therefore included herein.

Antibodies that are generated for use in the invention need not initially possess a particular desired isotype. Rather, the antibody as generated can possess any isotype and can be isotype switched thereafter using conventional techniques. These include direct recombinant techniques (see, e.g., U.S. Pat. No. 4,816,397), and cell-cell fusion techniques (see e.g., U.S. Pat. No. 5,916,771).

The effector function of the antibodies of the invention may be changed by isotype switching to an IgG1, IgG2, IgG3, IgG4, IgD, IgA, IgE, or IgM for various therapeutic uses. Furthermore, dependence on complement for cell killing can be avoided through the use of bispecifics, immunotoxins, or radiolabels, for example.

The invention also encompasses such antibodies as disclosed in, inter alia, International Patent Publication Nos. WO 00/37504 (published Jun. 29, 2000); WO 01/14424 (published Mar. 1, 2001); WO 93/00431 (published Jan. 7, 1993); and WO 00/32231 (published Jun. 8, 2000), among many others.

Although antibody 4.1.1, 4.13.1 and 11.2.1 are IgG2 antibodies, and 10D1 (ipilimumab) is an IgG1 antibody, and although the sequences of the variable regions of such antibodies are provided herein (see Table 3), and in the applications and patents referenced and incorporated herein, it is understood that the full-length sequences of these antibodies are encompassed herein, as well the use of any antibody comprising the sequences set forth in SEQ ID NOs:1 to 32, and further comprising any constant region, regardless of isotype as more fully discussed elsewhere herein.

Thus, the skilled artisan, once provided with the teachings provided herein, would readily appreciate that the methods and uses described herein include the use of a wide plethora of anti-CTLA4 antibodies and/or antigen-binding portions thereof.

Further, one skilled in the art, based upon the disclosure provided herein, would understand that the invention is not limited to administration of only a single antagonist; rather, the invention encompasses administering at least one CTLA4 antagonist, e.g. anti-CTLA-4 antibodies such as 4.1.1, 4.13.1, 11.2.1, and ipilimumab, in combination with at least one other therapeutic agent. Thus, any combination of CTLA4 antagonists can be combined with at least one therapeutic agent and the present invention encompasses any such combination and permutation thereof.

Therapeutic Methods

Therapeutic methods involve administering to a subject in need of treatment a therapeutically effective amount, or "effective amount", of an antibody, or antigen-binding portion, as contemplated by the present disclosure. As used herein, a "therapeutically effective", or "effective", amount refers to an amount of an antibody or portion thereof that is of sufficient quantity to result in a decrease in severity of disease symptoms, an increase in frequency and duration of disease symptom-free periods, prolongation of survival, and/or a prevention of impairment or disability due to the disease affliction—either as a single dose or according to a multiple dose regimen, alone or in combination with other agents. One of ordinary skill in the art would be able to determine such amounts based on such factors as the subject's size, the severity of the subject's symptoms, and the particular composition or route of administration selected. The subject may be a human or non-human animal (e.g., rabbit, rat, mouse, monkey or other lower-order primate).

An antibody or antigen-binding portion of the disclosure might be co-administered with known medicaments, and in some instances the antibody might itself be modified. For example, an antibody could be conjugated to an immunotoxin or radioisotope to potentially further increase efficacy. Regarding co-administration with additional therapeutic agents, such agents can include a cytotoxic agent, a radiotoxic agent or an immunosuppressive agent. The antibody can be linked to the agent (as an immunocomplex) or can be administered separately from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin can be intravenously administered as a 100 mg dose once every four weeks and adriamycin is intravenously administered as a 60 to 75 mg dose once every 21 days. Co-administration of the anti-CTLA4 antibodies, or antigen-binding portions thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

The antibodies and antigen-binding portions disclosed herein can be used as a therapeutic or a diagnostic tool in a variety of situations. Given the role that CTLA4 plays in the functioning of the immune system, disorders and conditions particularly suitable for treatment with an antibody or antigen-binding portion of the present disclosure include abnormal cell growth, for example, mesothelioma, hepatobilliary (hepatic and billiary duct), a primary or secondary CNS tumor, a primary or secondary brain tumor, lung cancer (NSCLC and SCLC), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, non-Hodgkin's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

To treat any of the foregoing disorders, pharmaceutical compositions for use in accordance with the present disclosure may be formulated in a conventional manner using one or more pharmaceutically acceptable carriers or excipients. An antibody or antigen-binding portion of the disclosure can be administered by any suitable means, which can vary, depending on the type of disorder being treated. Possible administration routes include parenteral (e.g., intramuscular, intravenous, intra-arterial, intraperitoneal, or subcutaneous), intrapulmonary and intranasal, and, if desired for local immunosuppressive treatment, intralesional administration. In addition, an antibody of the disclosure might be administered by pulse infusion, with, e.g., declining doses of the antibody.

In one embodiment, the dosing is given by injections, such as intravenous or subcutaneous injections, depending in part on whether the administration is brief or chronic. The amount to be administered will depend on a variety of factors such as the clinical symptoms, weight of the individual, and/or whether other drugs are administered. The skilled artisan will recognize that the route of administration will vary depending on the disorder or condition to be treated.

Determining a therapeutically effective amount of an antibody or antigen-binding portion according to the present disclosure will largely depend on particular patient characteristics, route of administration, and the nature of the disorder being treated. General guidance can be found, for example, in the publications of the International Conference on Harmonization and in Remington's Pharmaceutical Sciences, chapters 27 and 28, pp. 484-528 (18th ed., Alfonso R. Gennaro, Ed., Easton, Pa.: Mack Pub. Co., 1990). More specifically, determining a therapeutically effective amount will depend on such factors as toxicity and efficacy of the medicament. Toxicity may be determined using methods well known in the art and found in the foregoing references. Efficacy may be determined utilizing the same guidance in conjunction with the methods described below in the Examples.

For administration of the antibody or antigen-binding portion, the dosage can range from about 0.0001 to 100 mg/kg, and more usually 0.01 to 20 mg/kg, of the host body weight. For example dosages can be 0.3 mg/kg body weight, 1 mg/kg body weight, 3 mg/kg body weight, 5 mg/kg body weight, 10 mg/kg body weight, 15 mg/kg body weight, 20 mg/kg body weight, or within the range of 1 to 20 mg/kg. Exemplary treatment regimes include administration once per week, once every two weeks, once every three weeks, once every four weeks, once per month, once every 3 months or once every three to 6 months. Dosage regimens for an anti-CTLA antibody or antigen-binding portion thereof of the disclosure include, for example, 1 mg/kg body weight, 3 mg/kg body weight, 5 mg/kg body weight, 10 mg/kg body weight, 15 mg/kg body weight, or 20 mg/kg body weight via intravenous administration, with the antibody being given using one of the following dosing schedules: (i) every four weeks for six dosages, then every three months; (ii) every three weeks; (iii) 1-20 mg/kg body weight once followed by 1-20 mg/kg body weight every three weeks.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Example 1

Analysis of CRP in Patients Treated With Tremelimumab

The ability of serum C-reactive protein to predict survival benefit for patients treated with CTLA4 blockade was discovered in an analysis of data from clinical trial A3671009, a randomized multicenter Phase 3 study of tremelimumab versus chemotherapy (dacarbazine or temozolomide) in patients with previously-untreated, unresectable melanoma. Patients randomized to Arm A received intravenous tremelimumab at a dose of 15 mg/kg every 90 days for up to four doses. Patients randomized to Arm B received either dacarbazine at 1000 mg/m$^2$ or temozolomide at 200 mg/m$^2$ at the discretion of the investigator. The primary objective of the trial was to compare overall survival of patients in the two treatment arms. Objective tumor response was a secondary endpoint.

In the A3671009 trial, serum CRP was measured in most patients before initiation of treatment. In the analysis described below, baseline CRP refers to the result of a CRP assay performed on serum drawn from patients up to 14 days prior randomization into the study.

Table 1 shows the median overall survival (OS), the hazard ratios for survival for the two treatment arms, and the p-value for the difference in overall survival for the two treatment arms by CRP category. There was a clinically meaningful and statistically significant difference between treatment groups for patients with low baseline CRP (see FIG. 1). The hazard ratio of 1.48 represents a 48% improvement in overall survival in favor of patients who received CTLA4 blockade. There was no apparent difference between treatment groups in patients with high baseline CRP (see FIG. 2). This demonstrates that the group of patients with low CRP before treatment derives significant benefit from treatment with CTLA4 blockade as opposed to chemotherapy, while the group of patients with low baseline CRP does not appear to derive any survival benefit from treatment with CTLA4 blockade compared to chemotherapy.

TABLE 1

Overall Survival (OS) by CRP Category and by Treatment Arm

|  | Median OS CTLA4 blockade | Median OS Chemotherapy | P-value | HR |
|---|---|---|---|---|
| CRP ≦ 1.5 ULN | 19.1 months | 12.7 months | 0.0037 | 1.48 |
| CRP > 1.5 ULN | 6.1 months | 6.1 months | 0.3076 | 0.86 |

Table 2 shows the baseline characteristics of the patients in the low CRP group by treatment arm. The arms are well matched, except that there is a slightly higher percent of patients in Arm B with normal LDH and with ECOG performance status of 0; both of these factors are associated with good prognosis, favoring the chemotherapy arm. This indicates that the better survival of patients who received tremelimumab cannot be attributed to an imbalance of baseline factors between the two arms.

TABLE 2

Baseline characteristics of patients with low serum CRP per arm

| | CRP ≦ 1.5 | |
|---|---|---|
| | Arm A Tremelimumab | Arm B Chemotherapy |
| Females | 43.8% | 53.4% |
| Age >65 | 31.5% | 28.8% |
| Normal LDH | 73.8% | 78.8% |
| ECOG 0 | 75.4% | 80.5% |
| 1 site | 27.7% | 28.0% |
| 2 sites | 26.9% | 33.1% |
| ≧3 sites | 45.4% | 38.9% |
| Stage IV M1c* | 47.7% | 47.5% |
| Stage IV M1b* | 28.5% | 27.1% |
| Stage IV M1a* | 18.5% | 19.5% |
| Stage III* | 5.4% | 5.9% |

Figure 2:
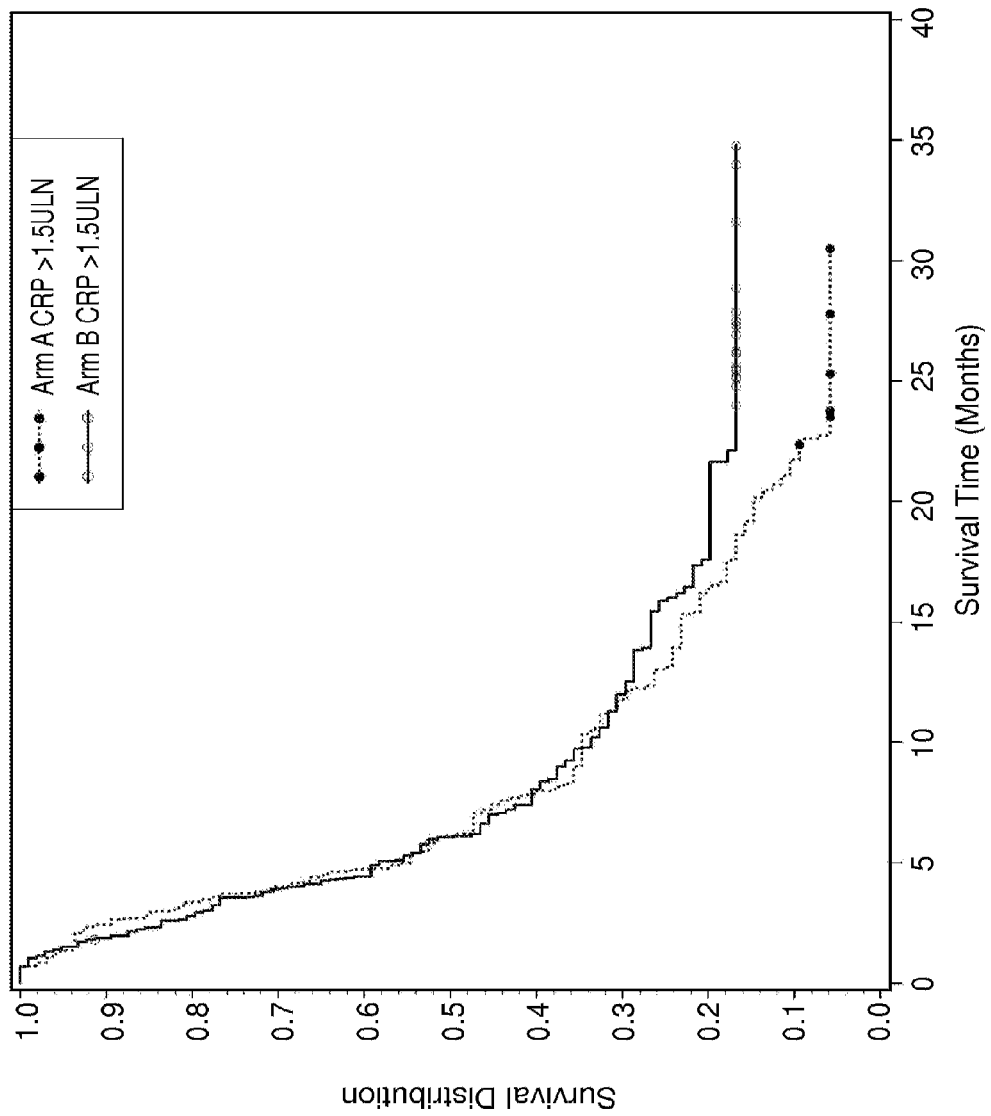
FIG. 2 shows a Kaplan Meier plot of overall survival from study A3671009 where the CRP level is >1.5 times the ULN in both treatment arms A and B.

*As set forth in the Cancer Staging Manual (6$^{th}$ Ed.), published by the American Joint Committee on Cancer FIGS. 1 and 2 show Kaplan Meier plots of overall survival by CRP category and by treatment Arm.

TABLE 3

Summary of Sequence Listing (H-CDR1 = heavy chain CDR1; L-CDR1 = light chain CDR1, etc; 4.1.1 = antibody 4.1.1 as described herein; 4.13.1 = antibody 4.13.1 as described herein; 11.2.1 = antibody 11.2.1 as described herein; 10D1 = antibody 10D1 as described herein; $V_H$ = variable heavy region; $V_L$ = variable light region;)

| SEQ ID NO | DESCRIPTION | SEQUENCE |
|---|---|---|
| 1 | 4.1.1 H-CDR1 | GFTFSHGMH |
| 2 | 4.1.1 H-CDR2 | VIWYDGRNKYYADSV |
| 3 | 4.1.1 H-CDR3 | GGHFGPFDY |
| 4 | 4.1.1 L-CDR1 | RASQSISSSFLA |
| 5 | 4.1.1 L-CDR2 | GASSRAT |
| 6 | 4.1.1 L-CDR3 | CQQYGTSPWT |
| 7 | 4.1.1 $V_H$ | GVVQPGRSLRLSCVASGFTFSSHGMHWVRQAPGKGLEWVAVIWYDGRNKYYADSVKGRFTISRDNSKNTLFLQMNSLRAEDTAVYYCARGGHFGPFDYWGQGTLVTVSSASTKGPSVFPLAPCSRSTSESTAALGCLVKDYFPEPVTVSWNSGALTSGVHTFPAVLQ |
| 8 | 4.1.1 $V_L$ | QSPGTLSLSPGERATLSCRASQSISSSFLAWYQQRPGQAPRLLIYGASSRATGIPDRFSGSGSGTDFTLTISRLEPEDFAVYYCQQYGTSPWTFGQGTKVEIKRTVAAPSVFIFPPSDEQLKSGTASVVCLLNNFYPREAK |
| 9 | 4.13.1 H-CDR1 | GFTFSSHGIH |
| 10 | 4.13.1 H-CDR2 | VIWYDGRNKDYADSV |
| 11 | 4.13.1 H-CDR3 | VAPLGPLDY |
| 12 | 4.13.1 L-CDR1 | RASQSVSSYLA |
| 13 | 4.13.1 L-CDR2 | GASSRAT |
| 14 | 4.13.1 L-CDR3 | CQQYGRSPFT |
| 15 | 4.13.1 $V_H$ | PGRSLRLSCAASGFTFSSHGIHWVRQAPGKGLEWVAVIWYDGRNKDYADSVKGRFTISRDNSKNTLYLQMNSLRAEDTAVYYCARVAPLGPLDYWGQGTLVTVSSASTKGPSVFPLAPCSRSTSESTAALGCLVKDYFPEPVTVSWNSGALTS |
| 16 | 4.13.1 $V_L$ | QSPGTLSLSPGERATLSCRASQSVSSYLAWYQQKPGQAPRLLIYGASSRATGIPDRFSGSGSGTDFTLTISRLEPEDFAVYYCQQYGRSPFTFGPGTKVDIKRTVAAPSVFIFPPSDEQLKSGTASVVCLLNNFYPREAKVQWKVD |
| 17 | 11.2.1 H-CDR1 | GFTFSSYGMH |
| 18 | 11.2.1 H-CDR2 | VIWYDGSNKYYADSV |
| 19 | 11.2.1 H-CDR3 | TAVYYCARDPRGATLYYYYYGMDV |
| 20 | 11.2.1 L-CDR1 | RASQSINSYLD |
| 21 | 11.2.1 L-CDR2 | AASSLQS |
| 22 | 11.2.1 L-CDR3 | QQYYSTPFT |
| 23 | 11.2.1 $V_H$ | GVVQPGRSLRLSCAASGFTFSSYGMHWVRQAPGKGLEWVAVIWYDGSNKYYADSVKGRFTISRDNSKNTLYLQMNSLRAEDTAVYYCARDPRGATLYYYYYGMDVWGQGTTVTVSSASTKGPSVFPLAPCSRSTSESTAALGCLVKDYFPEPVTVSWNSGALTSGVH |

TABLE 3-continued

Summary of Sequence Listing (H-CDR1 = heavy chain CDR1; L-CDR1 = light chain CDR1, etc; 4.1.1 = antibody 4.1.1 as described herein; 4.13.1 = antibody 4.13.1 as described herein; 11.2.1 = antibody 11.2.1 as described herein; 10D1 = antibody 10D1 as described herein; $V_H$ = variable heavy region; $V_L$ = variable light region;)

| SEQ ID NO | DESCRIPTION | SEQUENCE |
|---|---|---|
| 24 | 11.2.1 $V_L$ | PSSLSASVGDRVTITCRASQSINSYLDWYQ QKPGKAPKLLIYAASSLQSGVPSRFSGSGS GTDFTLTISSLQPEDFATYYCQQYYSTPFT FGPGTKVEIKRTVAAPSVFIFPPSDEQLKS GTASVVCLLNNFYPREAKV |
| 25 | 10D1 H-CDR1 | SYTMH |
| 26 | 10D1 H-CDR2 | FISYDGNNKYYADSVKG |
| 27 | 10D1 H-CDR3 | TGWLGPFDY |
| 28 | 10D1 L-CDR1 | RASQSVGSSYLA |
| 29 | 10D1 L-CDR2 | GAFSRAT |
| 30 | 10D1 L-CDR3 | QQYGSSPWT |
| 31 | 10D1 $V_H$ | QVQLVESGGGVVQPGRSLRLSCAASGFTFS SYTMHWVRQAPGKGLEWVTFISYDGNNKYY ADSVKGRFTISRDNSKNTLYLQMNSLRAED TAIYYCARTGWLGPFDYWGQGTLVTVSS |
| 32 | 10D1 $V_L$ | EIVLTQSPGTLSLSPGERATLSCRASQSVG SSYLAWYQQKPGQAPRLLIYGAFSRATGIP DRFSGSGSGTDFTLTISRLEPEDFAVYYCQ QYGSSPWTFGQGTKVEIK |

The invention claimed is:

1. A method of treating melanoma, comprising the steps of:
 a) selecting a subject with a serum CRP concentration that is less than or equal to 1.5 times the upper-limit-of-normal value; and
 b) administering an anti-CTLA4 antibody or an antigen-binding portion thereof to said subject.

2. A method of treating melanoma, comprising the steps of:
 a) determining the serum CRP concentration in a subject in a CRP assay;
 b) selecting a subject with a serum CRP concentration that is less than or equal to 1.5 times the upper-limit-of-normal value as determined by said CRP assay; and
 c) administering an anti-CTLA4 antibody or an antigen-binding portion thereof to the selected subject.

3. A method of predicting a benefit to a melanoma patient of an immunotherapy treatment using an anti-CTLA-4 antibody or an antigen-binding portion thereof, over a chemotherapy treatment, comprising: a) measuring the serum CRP concentration in the patient in a CRP assay; b) comparing said serum CRP concentration to the upper-limit-of-normal (ULN) value as determined by the CRP assay, wherein a serum CRP concentration in the patient of less than or equal to 1.5 times the ULN value is indicative of a benefit to the patient of the immunotherapy treatment over a chemotherapy treatment.

4. The method of claim 3, wherein the benefit is an improvement in overall survival.

5. The method of claim 1 or 3, wherein said melanoma is unresectable stage IV melanoma.

6. The method of claim 1 or 3, wherein said anti-CTLA4 antibody comprises the heavy and light chain CDR sequences set forth in SEQ ID NOs: 17, 18, 19, 20, 21, and 22.

7. The method of claim 1 or 3, wherein said anti-CTLA4 antibody comprises the heavy and light chain CDR sequences set forth in SEQ ID NOs: 25, 26, 27, 28, 29, and 30.

8. The method of claim 6, wherein said antibody is tremelimumab.

9. The method of claim 7, wherein said antibody is ipilimumab.

10. The method of claim 1 or 3, wherein said anti-CTLA4 antibody comprises the heavy and light chain CDR sequences set forth in:
 a) SEQ ID NOs: 1, 2, 3, 4, 5, and 6; or
 b) SEQ ID NOs: 9, 10, 11, 12, 13, and 14.

11. The method of claim 1 or 3, wherein said anti-CTLA4 antibody comprises a heavy chain comprising the amino acid sequence of SEQ ID NO: 7 and a light chain comprising the amino acid sequence of SEQ ID NO: 8.

12. The method of claim 1 or 3, wherein said anti-CTLA4 antibody comprises a heavy chain comprising the amino acid sequence of SEQ ID NO: 15 and a light chain comprising the amino acid sequence of SEQ ID NO: 16.

13. The method of claim 1 or 3, wherein said anti-CTLA4 antibody comprises a heavy chain comprising the amino acid sequence of SEQ ID NO: 23 and a light chain comprising the amino acid sequence of SEQ ID NO: 24.

14. The method of claim 1 or 3, wherein said anti-CTLA4 antibody comprises a heavy chain comprising the amino acid sequence of SEQ ID NO: 31 and a light chain comprising the amino acid sequence of SEQ ID NO: 32.

* * * * *